United States Patent [19]

McCarty

[11] Patent Number: 5,073,374
[45] Date of Patent: Dec. 17, 1991

[54] FAST DISSOLVING BUCCAL TABLET
[75] Inventor: John A. McCarty, Biscayne Park, Fla.
[73] Assignee: Schering Corporation, Kenilworth, N.J.
[21] Appl. No.: 278,099
[22] Filed: Nov. 30, 1988
[51] Int. Cl.$^5$ .................. A61K 9/20; A61K 47/00
[52] U.S. Cl. ...................... 424/435; 424/434; 424/464; 424/465; 514/777
[58] Field of Search ............... 424/434, 435, 465, 499

[56] References Cited

U.S. PATENT DOCUMENTS

| | | | |
|---|---|---|---|
| 4,059,686 | 11/1977 | Tanaka et al. | 424/19 |
| 4,226,848 | 10/1980 | Naggi et al. | 424/19 |
| 4,292,299 | 9/1981 | Suzuki et al. | 424/16 |
| 4,572,832 | 2/1986 | Kigasawa et al. | 424/19 |
| 4,755,386 | 7/1988 | Hsiao et al. | 424/435 |

FOREIGN PATENT DOCUMENTS

| | | |
|---|---|---|
| 2175853 | 10/1973 | France . |
| 1380171 | 1/1975 | United Kingdom . |
| 2188843 | 10/1987 | United Kingdom . |
| 04342 | 7/1987 | World Int. Prop. O. .......... 424/435 |

OTHER PUBLICATIONS

Kornbloom and Stoopak, J. Pharm. Sci., 62:43-49 (1973).
Kahn and Rooke, Mfg. Chemist & Aerosol News, pp. 25-26 (Jan. 1976).
Kahn and Rooke, J. Pharm. Pharmacol., 28:633-636 (1976).

Primary Examiner—Thurman K. Page
Assistant Examiner—James M. Spear
Attorney, Agent, or Firm—Anita W. Magatti; James R. Nelson

[57] ABSTRACT

A fast dissolving buccal tablet for administering a medicament includes the active ingredient, a lubricant and a water soluble sugar, such as sorbitol, combined such that the buccal tablet dissolves in about one minute.

10 Claims, No Drawings

FAST DISSOLVING BUCCAL TABLET

SUMMARY

This invention is directed to a buccal tablet comprising an effective amount of an active ingredient in combination with an excipient, the excipient being comprised essentially of sorbitol and a lubricant. The tablet provides extremely rapid drug delivery in an unexpected manner, giving blood levels which are comparable to parenteral administration of the active ingredient.

BACKGROUND OF THE INVENTION

This application is directed to a tablet for the buccal administration of an active ingredient. Buccal administration (in the pouch of the cheek of the subject) is particularly useful for active ingredients which show poor bioavailability upon administration through other non-parenteral modes. This poor availability can be attributed to low solubility, degradation by enzymes or destruction by acid upon passing through the intestinal tract, or first pass destruction by the liver enzymes after absorption from the gastrointestinal tract. Examples of such medicaments include: steroids such as estrogens. e.g. estradiol and derivatives such as the salt and valerate, cypionate or propionate forms; progestins, e.g. progesterone and related compounds, androgens and anabolic steroids; propranolol; thyroid hormones; analgesics such as morphine and morphine derivatives, fentanyl and sulfentanil; ergotamine derivatives (for migraine therapy); bromocriptine (for treating parkinsons disease); pH sensitive peptides and small proteins such as insulin and ACTH; physostigmine; scopolamine; verapamil; and gallopamil. It is also possible to administer compounds having good oral bioavailability buccally, but normally such medicaments would be administered orally for convenience.

Buccal administration of estradiol gives an unexpected early peak in the blood level followed by a slowly decreasing concentration. This tracks the natural occurrence of estradiol in the body, and thus is an improvement over transdermal administration, which provides a relatively constant blood level. Oral administration of estrogens such as estradiol is impractical in view of the destruction of the active ingredient in the liver shortly after absorption from the gastrointestinal tract.

Most buccal formulations are designed to provide sustained release of the active, thereby avoiding swallowing of the active ingredient due to disintegration of the dosage form. Other buccal formulations utilize a disintegrant to accelerate buccal tablet disintegration. Such disintegrants include polyvinylpyrrolidone, starch, alginic acid, formaldehyde, calcium carboxymethyl cellulose, sodium starch glycolate, and sodium carboxymethyl cellulose as disclosed in Kornblum and Stoopak, J. Pharm. Sciences 62: 43-49 (1973); U.S. Pat. No. 1,380,171; Khan and Rooke, Mfg. Chemist & Aerosol News (Jan. 1976); and Khan and Rooke, J. Pharm. Pharmac. 28: 633-636 (1976).

Applicant has discovered a fast buccal formulation which rapidly delivers the active ingredient through the buccal route in an unexpected manner. Such a rapid delivery from a buccal formulation is useful for delivering a bolus dose to achieve a rapid rise in blood levels. Moreover, the rapid delivery of the drug from the buccal tablets unexpectedly obviates the need for an adhesive, which is required in other buccal tablets to prevent the patient from swallowing the dosage form. Such adhesive containing buccals are disclosed, for example. in U.S. Pat. No. 4,755,386, U.S. Pat. No. 4,059,686, U.S. Pat. No. 4,292,299, and U.S. Pat. No. 4,226,848.

DETAILED DESCRIPTION OF THE INVENTION

The fast dissolving buccal formulation may include essentially three components: the buccally absorbable active ingredient(s), a pharmaceutically acceptable lubricant and a soluble, directly compressible tablet excipient.

The soluble excipient is typically a sugar, such as sucrose or lactose. The preferred sugar is sorbitol, and in particular, sorbitol N.F. and/or spray dried sorbitol in an amount ranging from about 90 to 99 percent. The soluble excipients also include vehicles for hydrophobic actives. Such vehicles include solids which melt at about room temperature and surfactants. The concept is to use these vehicles to improve the dissolution of insoluble drugs either by micellar solubilization in a surfactant or by having a solid, in which the drug is soluble, which liquifies at body temperature or by using a combination of such surfactants and solids. Suitable surfactants include pluronic, Tweens, sodium lauryl sulfate, and the like and suitable liquifying solids include the various polyethylene glycols, low melting glycerides (preferably melting at about 25° to 45° C.), and various suppository bases, which are known to one skilled in the art.

The lubricant used in the fast buccal formulation may be any conventional lubricant, such as magnesium stearate or sodium dodecyl sulfate. Generally, the lubricant should be water soluble. Hence, the preferred lubricant is sodium dodecyl sulfate in an amount ranging from about 1 to 3 percent.

The active ingredients useful in the invention include those mentioned in the background of the invention. The amount contained will vary, depending upon the desired dosage for a given treatment. Estradiol, when used as the active ingredient, is present in an amount ranging from about 50 micrograms to about 2 mgs per tablet.

The formulations of the present invention can be prepared by simply mixing the ingredients together and compressing desired amounts of the mixture into tablet form. The final formulations desirably have a diameter of about a quarter inch (0.635 cm) and a thickness of about 0.05 inches (0.127 cm), and upon administration disintegrate in about 30 seconds to around 5 minutes, and preferably in about one minute.

The present invention is illustrated by the following non-limiting examples.

EXAMPLE 1

The following ingredients are blended using a V-Blender with an intensifier bar and mixed for about five to ten minutes.

| % BY WEIGHT | INGREDIENT | AMOUNT |
| --- | --- | --- |
| 0.2 | Estradiol, USP | 2.0 g |
| 98.8 | Sorbitol N.F. | 988.0 g |
| 1.0 | Sodium Dodecyl Sulfate | 10.0 g |
| 100.00 | | |

Tablets weighing about 0.05 gm./tablet are formed using a compression force of about 1000 PSI. The batch yields about 20,000 tablets which upon administration disintegrate in about one minute. The tablets are about 1/4 inch in diameter.

EXAMPLE 2

Using the procedure described above in Example 1, buccal tablets are prepared using the excipients described below in Table 1. Each tabletting operation is performed using a 500, 1000 or 2000 psi compression force as appropriate. In vitro disintegration results indicate that each formulation produces buccal tablets which dissolve in approximately one minute. The quantity of sorbitol described below must be reduced to allow for the addition of active ingredient. For example, a typical quantity of estradiol would be 0.2% by weight, so the quantity of sorbitol would be reduced by 0.2%. If a different active ingredient is used, e.g., scopolamine, the content of sorbitol is reduced accordingly.

TABLE 1

| Sorbitol N.F. (% w/w) | Magnesium Stearate (% w/w) | Sodium Dodecyl Sulfate (% w/w) |
|---|---|---|
| 98.0 | 0 | 2.0 |
| 97.0 | 0 | 3.0 |
| 98.8 | 0.2 | 1.0 |
| 97.8 | 0.2 | 2.0 |
| 96.8 | 0.2 | 3.0 |
| 98.5 | 0.5 | 1.0 |
| 97.5 | 0.5 | 2.0 |
| 96.5 | 0.5 | 3.0 |

EXAMPLE 3

Substitute spray-dried sorbitol for sorbitol N.F. in the above example in a formulation containing the excipients shown below in Table 2 and utilize the procedure of example 1 to produce buccal tablets which deliver the active ingredient in approximately one minute.

TABLE 2

| Spray Dried Sorbitol (% w/w) | Magnesium Stearate (% w/w) | Sodium Dodecyl Sulfate (% w/w) |
|---|---|---|
| 96.8 | 0.2 | 3.0 |
| 97.5 | 0.5 | 2.0 |

Based upon the formulation and disintegration data above, the fast buccal tablets described herein will deliver the buccally absorbable active ingredient to a patient in need of such treatment in approximately one minute.

To administer the active ingredient in conformance with the invention described herein, a fast buccal tablet is simply placed in the buccal pouch of the oral cavity, and allowed to dissolve. The drug is delivered systemically upon dissolution.

The rapid delivery of a drug in this manner is particularly important wherever rapid onset of action is required. For example, rapid administration of scopolamine for easing the physical discomfort of motion sickness is one preferred application. Similarly, rapid delivery of estradiol is important in that the pharmacokinetics achieved mimic the naturally occuring release and elimination of female hormones.

While a detailed description and certain preferred embodiments of the invention have been provided above, the present invention is not limited thereto, but rather is defined in the following claims.

I claim:

1. A buccal tablet comprising an effective amount of a buccally absorbable active ingredient, a water soluble buccal tablet excipient selected from the group consisting of sucrose, lactose and sorbitol present in an amount ranging from 90 to 99 percent of the tablet weight, and a pharmaceutically acceptable lubricant wherein the lubricant is magnesium stearate or sodium dodecyl sulfate in an amount ranging from 1 to 3 percent of the tablet weight and wherein the lubricant is chosen so that disintegration occurs from 0.5 to 5 minutes after administration.

2. A buccal tablet as defined in claim 1 wherein the water soluble buccal tablet excipient is sorbitol.

3. A buccal tablet as defined in claim 2 wherein the lubricant is sodium dodecyl sulfate.

4. A buccal tablet as defined in claim 1 wherein the active ingredient is estradiol.

5. A buccal tablet as described in claim 1 wherein the active ingredient is scopolamine.

6. A buccal tablet as described in claim 1 wherein the active ingredient is present in an amount ranging from about 50 micrograms to about 2 milligrams.

7. A buccal tablet as described in claim 3 wherein the active ingredient is estradiol.

8. A buccal tablet as defined in claim 3 wherein the active ingredient is scopolamine.

9. A buccal tablet as defined in claim 3 wherein the active ingredient is present in an amount ranging from about 50 micrograms to about 2 milligrams.

10. A buccal tablet as defined in claim 9 wherein the active ingredient is estradiol.

* * * * *